United States Patent [19]

Hök

[11] Patent Number: 4,712,566

[45] Date of Patent: Dec. 15, 1987

[54] DEVICE FOR RECORDING PHYSIOLOGICAL PRESSURES

[75] Inventor: Bertil Hök, Västerås, Sweden

[73] Assignee: Radisensor AB, Västerås, Sweden

[21] Appl. No.: 915,066

[22] PCT Filed: Jan. 9, 1986

[86] PCT No.: PCT/SE86/00005

§ 371 Date: Sep. 5, 1986

§ 102(e) Date: Sep. 5, 1986

[87] PCT Pub. No.: WO86/03956

PCT Pub. Date: Jul. 17, 1986

[30] Foreign Application Priority Data

Jan. 10, 1985 [SE] Sweden ............................. 8500104

[51] Int. Cl.⁴ .............................................. A61B 5/00
[52] U.S. Cl. .................................. 128/748; 128/673; 73/4 R
[58] Field of Search ............................. 128/672–675, 128/748, 664–667, 774; 73/4 R, 753, 756

[56] References Cited

U.S. PATENT DOCUMENTS

| | | | |
|---|---|---|---|
| 3,088,323 | 5/1963 | Welkowitz et al. | 128/715 X |
| 4,413,528 | 11/1983 | Hok et al. | 128/673 X |
| 4,459,841 | 7/1984 | Hok et al. | 128/673 X |
| 4,543,965 | 10/1985 | Pack et al. | 128/748 |

Primary Examiner—Kyle L. Howell
Assistant Examiner—Angela D. Sykes
Attorney, Agent, or Firm—Witherspoon & Hargest

[57] ABSTRACT

A device for physiological pressure monitoring comprises a miniaturized pressure sensor element which is located near the tip of a guide, which in turn is inserted into a catheter. The guide and the catheter have sealing surfaces which can be brought into contact with each other by axial or rotary motion of the guide in relation to the catheter, whereby the sensor element becomes available for calibration from a pressure generator connected to the catheter.

20 Claims, 7 Drawing Figures

DEVICE FOR RECORDING PHYSIOLOGICAL PRESSURES

BACKGROUND OF THE INVENTION

1. Field Of The Invention

Physiological pressure measurement is a classical technical problem to which no acceptable solutions have been found in spite of considerable effort. It is commonly known to use liquid-filled catheters for providing hydraulic communication between the signal source (the body fluid) and the pressure sensor, which converts the hydrostatic pressure signals into electrical output signals. However, the hydraulic transfer in the catheter has severe limitations as regards the bandwidth (typically about ten Hz) and because of artifacts due to acceleration of the mass of liquid contained in the catheter.

2. Description of the Prior Art

These problems can be solved by miniaturizing the pressure sensor so that it can be located immediately at the signal source. A plurality of technical solutions of this problem have been suggested, making use of inductive, piezoresistive, capacitive or fiber optical pressure sensor elements. Certain types have also become available on the market and are to a certain extent used in animal tests and urological examinations in which the measuring practice and the hygienic requirements are less severe than for use in the heart and vessel system.

The reason for the limited use of miniaturized pressure sensors is primarily their inferior reliability, in combination with the fact that they usually have not been sufficiently adapted for standard clinical routines as regards possibilities of sterilization, compatability with other equipment, etc.

It is an object of the present invention to solve the above mentioned and related problems. A salient feature of the device according to the invention is that the miniaturized sensor element at any time during an ongoing examination can be tested against an externally generated calibration pressure. This offers a considerably increased reliability of the system compared to the prior art solutions. The device according to the invention includes at least one valve function capable of shutting off the signal pressure and instead connecting the calibration pressure. The valve function should be remotely controlled since repeated insertion and withdrawal of the sensor element would discomfort the patient, increase the risks of contamination and infectious hazards and require an increased x-ray dosage and cause other undesired effects. In the present invention the critical valve function is achieved by mechanical means, which has proven to result in a safer and more reliable function than alternative solutions making use of hydraulic or electromechanical control. The use of an automatic or semi-automatic calibration function further reduces the requirements on linearity, temperature stability and long term stability on the sensor element, which consequently can be of simpler design and have smaller dimensions. The latter increases the usefulness considerably since a larger number of body vessels become available for examination. An example thereof are the coronary vessels, in which pressure measurements can provide adequate information about stenosis and coverings. This would improve the possibilities of diagnosing and treating patients being in the danger-zone of having a myocardial infarction.

SUMMARY OF THE INVENTION

The invention thus provides a device for recording physiological pressures, comprising an essentially threadlike guide (3) capable of being inserted into a catheter (4), and at least one sensor element (1) provided near the tip of the guide (3), said at least one sensor element (1) producing an electrical or optical signal representing the hydrostatic pressure prevailing at the sensor element, which is characterized in that the guide (3) and the catheter (4) have at least one sealing surface (5, 6; 15, 16) each, which open and shut-off the hydraulic communication between the sensor element (1) and its surrounding medium by means of axial or rotary motion of the guide (3) in relation to the catheter (4), whereby the sensor element (1), via the interior of the catheter (4), can be brought into pressure communication with a pressure generator (7) connected to the proximal end of the catheter (4), said pressure generator being arranged to generate and transmit known calibration pressures to the sensor element (1).

BRIEF DESCRIPTION OF THE DRAWINGS

The invention will be explained in more detail with reference to the enclosed drawings, in which.

DESCRIPTION OF THE PREFERRED EMBODIMENTS

Figure 1:
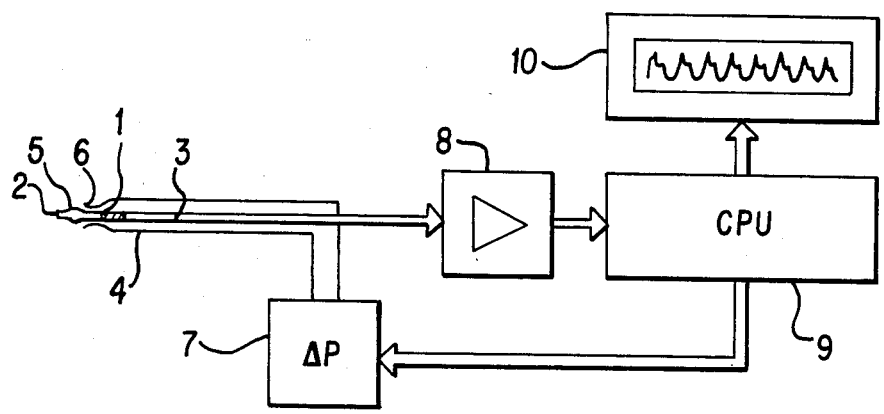
FIG. 1 is a block diagram illustrating the system according to the invention.

FIG. 1 shows the principal design of the system. A pressure sensor element 1 is located close to the tip 2 of a threadlike guide 3, which also comprises means for the transmission of signals from the sensor element 1 and for the supply of energy to the sensor element. In the simpliest embodiment both of these two functions are achieved by means of an optical fibre, but an electrical wire connection can, of course, be used as an alternative. The signals are transferred to a converting and amplifying unit 8, in which the original pressure signal is converted into an analogue or digital electric signal. Filtering or any other suitable signal processing takes place in a central signal processing and control unit 9, which in a typical embodiment comprises a micro processor having a program memory for sequential control of the function. The signal is then applied to a presentation/memory unit 10, e.g. consisting of a printer or a tape recorder. The guide 3 is inserted into a tubular catheter 4. Both the guide 3 and the catheter 4 comprise matching sealing surfaces 5, 6 so that the hydraulic communication between the sensor element 1 and the signal source (i.a. the medium surrounding the front, distal part of the catheter) can be opened or closed. To this end the guide 3 is movable in relation to the catheter 4 and can be displaced axially or be rotated. When the sealing surfaces 5 and 6 are brought into mechanical contact, the communication between the signal source and the sensor element 1 is shut off. The sensor element 1 will when instead be available for the application of a calibration pressure via the catheter, the rear (proximal) part of which is connected to a pressure generator 7. Controlled by the control unit 9 the pressure generator 7 generates a known hydrostatic pressure for calibration of the transferring function of the sensor element 1. In the simpliest embodiment the pressure generator 7 is a liquid column of variable height or, alaternatively, an electromechanical pump having a pressure regulator.

Figure 2:
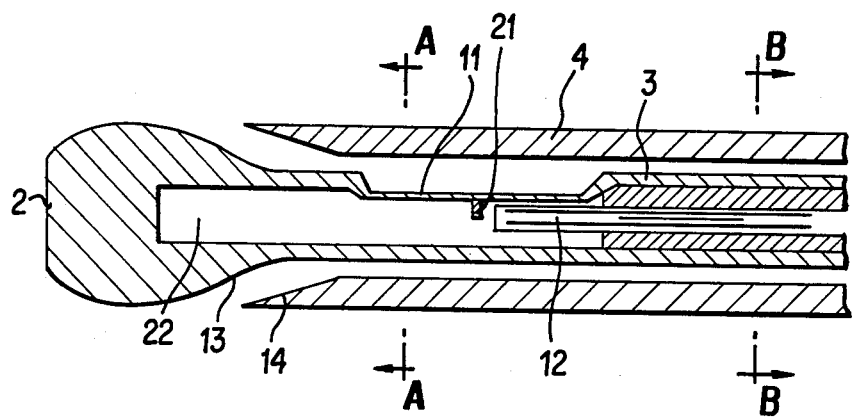
FIGS. 2, 2a, 2b and 3, 3a illustrate two alternative embodiments of the sensor element and the essential valve function.
Figure 2A:
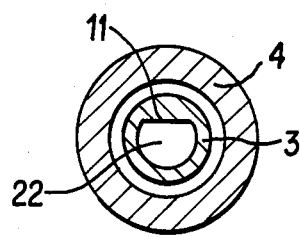
Figure 2B:
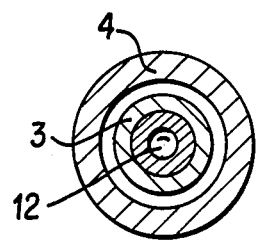

FIGS. 2, 2a, 2b in greater detail show an embodiment of the sensor element 1 and the critical valve action of the sealing surfaces 5 and 6. The sensor element 1 communicates with the amplifying unit 8 by means of an optical fibre 12. A mirror 21 is mounted on a membrane 11 close to the end surface of the optical fibre 12. Elastic movements of the membrane are created on pressure variations. In response thereto the mirror element 21 is displaced in relation to the fibre 12, thereby effecting the intensity of the light reflected back into the fibre 12. In this embodiment the amplifying unit 8 comprises both a light source and a light detector in optical connection with the fibre 12. The light detector then produces an electrical signal, which is an unambiguous function of the hydrostatic pressure at the sensor element 1. The membrane 11 consists of a thin foil, for example made of a metallic or semi-conducting material, which has been secured to the envelope surface of the guide 3, e.g. by welding or gluing. A cavity 22 has been provided, which either consists of a closed gas-filled or evacuated chamber or communicates along the entire length of the guide so as to equalize the pressure between the surrounding air and the cavity 22. In the simpliest embodiment the sealing surface 5 on the guide 3 and the sealing surface 6 on the catheter 4 comprise conical sections, which provide a reliable sealing function when the surfaces 5 and 6 are brought together by axial displacement. At least one of the surfaces 5 and 6 is preferably coated with a soft rubbery material such as silicone or polyurethane. In a variant the sealing surface 5 on the guide 3 is designed as an inflatable balloon in pressure communication along the entire length of the guide 3. Such an embodiment has the advantage that one and the same guide 3 can be used together with catheters 4 of varying inner diameters and yet give a satisfying sealing function between the surfaces 5 and 6.

Figure 3:
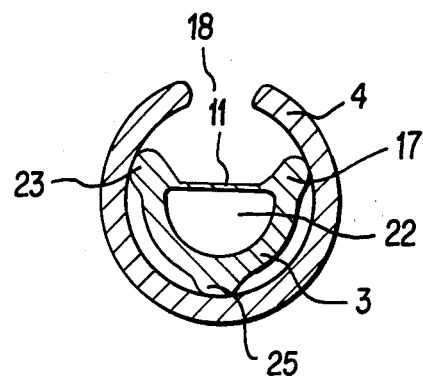
Figure 3A:
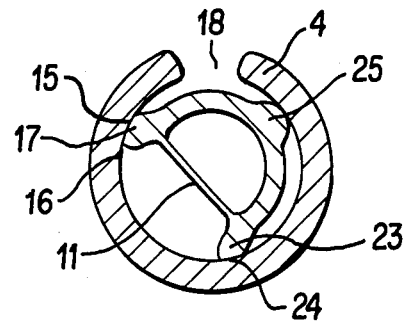

FIGS. 3, 3a show an alternative embodiment of the critical valve function, wherein the valve is controlled by means of a rotary motion instead of the axial motion illustrated in FIGS. 2, 2a, 2b. In the cross-sections through the guide 3 and the catheter 4 FIG. 3a illustrates the measuring and FIG. 3b the calibration position. The membrane 11 separating the cavity 22 from the surrounding is shown. The guide 3 is provided with axially extending flanges 17, 23, 25, which extend over the entire length of the guide 3 and serve as sealing elements in that the surfaces 15, 24 of the flanges contact the inner wall 16 of the catheter 4. The catheter 4 has a lateral opening 18 permitting pressure communication between the membrane 8 and the surrounding environment when the membrane 11 is directed towards the lateral opening 18. Said communication is interrupted by rotating the guide from the position of FIG. 3 to the position shown in FIG. 3b.

Figure 4:
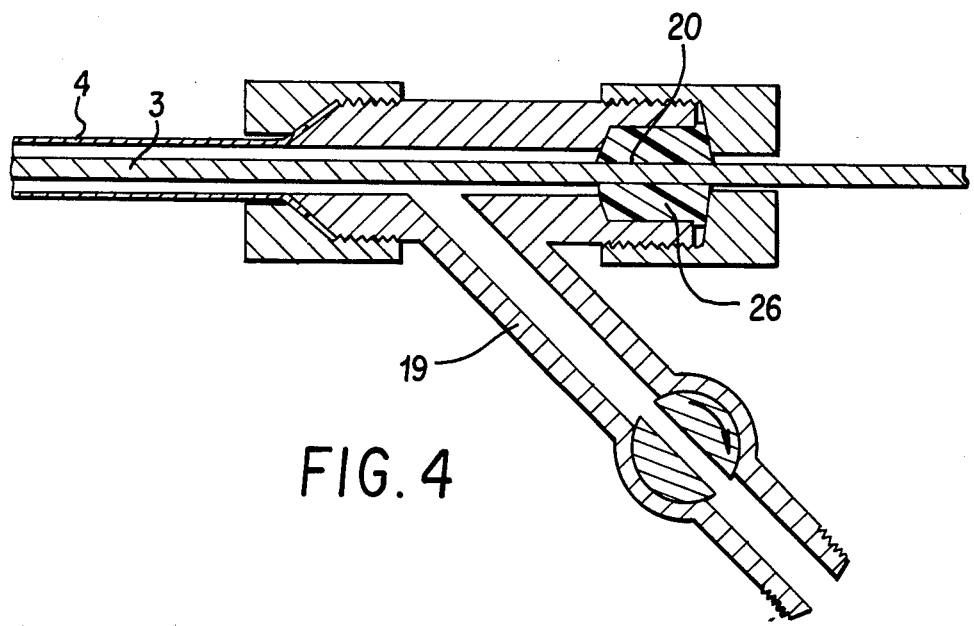
FIG. 4 is a schematic sectional view illustrating a further valve element belonging to the system.

FIG. 4 shows a further valve function located at the rear (proximal) part of the catheter. This valve 19 can alternatingly establish and shut-off the pressure communication to the pressure generator 7. The valve 19 can either be manually operated or be controlled by e.g. an electromechanical driving device. The valve 19 further comprises a pressure tight lead-through 20 for the guide 3. The lead-through 20 permits the axial or rotary motions of the guide 3 relative to the catheter 4 which are required on calibration without any undue leakage. The sealing function of the lead-through 20 is provided by a compressed gasket 26, e.g. consisting of a soft rubbery material such as silicone.

The invention can be varied in many ways within the scope of the following claims.

I claim:

1. A device for recording physiological pressures, comprising an essentially threadlike guide (3) inserted into a catheter (4), and at least one sensor element (1) provided near the tip of the guide (3), said at least one sensor element (1) producing an electrical or optical signal representing the hydrostatic pressure prevailing at the sensor element, characterized in that the guide (3) and the catheter (4) have at least one sealing surface (5, 6; 15, 16) each which are brought into contact with each other and which open and shut-off the hydraulic communication between the sensor element (1) and its surrounding medium by means of axial or rotary motion of the guide (3) in relation to the catheter (4), whereby the sensor element (1), via the interior of the catheter (4), can be brought into pressure communication with a pressure generator (7) connected to a proximal end of the catheter (4), said pressure generator being arranged to generate and transmit known calibration pressures to the sensor element (1).

2. A device according to claim 1, characterized in that the sensor element (1) is provided with at least one elastic membrane (11), the deflection of which is monotonically associated with the hydrostatic pressure to be measured.

3. A device according to claim 2, including a signal converting and amplifying unit (8) which converts the signals generated from the sensor element (1) into analogue or digital electrical signals, said signals bieng processed in at least one signal processing and control unit (9), which in turn adjusts the signals to a suitable form of presentation in a presentation or memory unit (10), e.g. consisting of a printer, a tape-recorder or the like, and in that said signal processing and control unit (9) transmits control signals to said pressure generator (7).

4. A device according to claim 2 characterized in that the guide (3) comprises at least one optical fibre (12) or electrically conducting wire.

5. A device according to claim 2 characterized in that at least one of said sealing surfaces (5,6) is formed by at least one conical section (13, 14) provided on the guide (3) or on the catheter (4).

6. A device according to claim 2 characterized in that the sealing surfaces (15, 16) are formed by at least one flange (17) provided on the guide (3) or on the catheter (4).

7. A device according to claim 1 including a signal converting and amplifying unit (8) which converts the signals generated from the sensor element (1) into analogue or digital electrical signals, said signals being processed in at least one signal processing and control unit (9), which in turn adjusts the signals to a suitable form of presentation in a presentation or memory unit (10), e.g. consisting of a printer, a tape-recorder or the like, and in that said signal processing and control unit (9) transmits control signals to said pressure generator (7).

8. A device according to claim 7 characterized in that the guide (3) comprises at least one optical fibre (12) or electrically conducting wire.

9. A device according to claim 7 characterized in that at least one of said sealing surfaces (5, 6) is formed by at least one conical section (13, 14) provided on the guide (3) or on the catheter (4).

10. A device according to claim 7 characterized in that the sealing surfaces (15, 16) are formed by at least one flange (17) provided on the guide (3) or on the catheter (4).

11. A device according to claim 1, characterized in that the guide (3) comprises at least one optical fibre (12) or electrically conducting wire.

12. A device according to claim 11 characterized in that at least one of said sealing surfaces (5, 6) is formed by at least one conical section (13, 14) provided on the guide (3) or on the catheter (4).

13. A device according to claim 11 characterized in that the sealing surfaces (15, 16) are formed by at least one flange (17) provided on the guide (3) or on the catheter (4).

14. A device according to claim 1 characterized in that at least one of said sealing surfaces (5, 6) is formed by at least one conical section (13, 14) provided on the guide (3) or on the catheter (4).

15. A device according to claim 1 characterized in that the sealing surfaces (15, 16) are formed by at least one flange (17) provided on the guide (3) or on the catheter (4).

16. A device according to claim 15 characterized in that the catheter (4) has at least one lateral opening (18).

17. A device according to claim 1 characterized in that the catheter (4) has at least one lateral opening (18).

18. A device according to claim 17 characterized in that at least one manually electromechanically controlled valve (19) is connected to the proximal end of the catheter (4), said valve (19) being capable of opening and shutting off the hydraulic communication between the interior of the catheter (4) and the pressure generator (7), and in that said valve (19) also comprises a leak-tight lead-through (20) for the guide (3).

19. A device according to claim 1 characterized in that at least one manually or electromechanically controlled valve (19) is connected to the proximal end of the catheter (4), said valve (19) being capable of opening and shutting off the hydraulic communication between the interior of the catheter (4) and the pressure generator (7), and in that said valve (19) also comprises a leak-tight lead-through (20) for the guide (3).

20. A device according to claim 1 characterized in that at least one of said sealing surfaces (5, 6) has the form of an inflatable balloon which is in pressure communication along the length of the guide (3) or the catheter (4).

* * * * *